US007955842B2

(12) United States Patent
Lee et al.

(10) Patent No.: US 7,955,842 B2
(45) Date of Patent: Jun. 7, 2011

(54) MICROFLUIDIC DEVICE AND METHOD FOR CONCENTRATING SAMPLE CONTAINING CELLS OR VIRUSES AND LYSING CELLS OR VIRUSES, AND METHOD OF PRODUCING THE MICROFLUIDIC DEVICE

(75) Inventors: Hun-joo Lee, Yongin-si (KR); Joon-ho Kim, Yongin-si (KR); Sung-young Jeong, Yongin-si (KR); Kyu-youn Hwang, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 1162 days.

(21) Appl. No.: 11/670,002

(22) Filed: Feb. 1, 2007

(65) Prior Publication Data
US 2007/0237680 A1    Oct. 11, 2007

(30) Foreign Application Priority Data

Apr. 7, 2006 (KR) .................. 10-2006-0031931

(51) Int. Cl.
*C12M 1/42* (2006.01)
*C12M 1/33* (2006.01)
(52) U.S. Cl. .............. 435/306.1; 435/287.1; 205/755
(58) Field of Classification Search .................. 205/755; 435/306.1, 259, 287.1, 5
See application file for complete search history.

(56) References Cited

U.S. PATENT DOCUMENTS

| 5,006,108 | A * | 4/1991 | LaPrade | 604/20 |
| 6,436,264 | B1 * | 8/2002 | Tamura | 204/634 |
| 7,488,596 | B2 * | 2/2009 | Lee et al. | 435/306.1 |
| 7,582,329 | B2 * | 9/2009 | Schmitz et al. | 427/115 |

| 2003/0075446 | A1 | 4/2003 | Culbertson et al. | |
| 2006/0057448 | A1 * | 3/2006 | Miyauchi et al. | 429/30 |
| 2006/0134777 | A1 * | 6/2006 | Lee et al. | 435/306.1 |

FOREIGN PATENT DOCUMENTS

| EP | 1541234 | 12/2003 |
| EP | 1672459 | 11/2005 |
| WO | 02/12896 | 2/2002 |
| WO | 2006/036307 | 4/2006 |

OTHER PUBLICATIONS

Hasenbein, M.E., et al., "Micropatterned surfaces modified with select peptides promote exclusive interactions with osteoblasts" Biomaterials, vol. 23, 2003, p. 3937-3942.*
Palladium-hydrogen electrodes for coulmoetric titration analysis of acids and bases; Bhadra Munasiri, Jillian Cockburn, Keith A. Hunter; J. Electroanal. Chem., 332 (1992) 333-337.
European Search Report; EP1541234A1; WO02/12896A; EP1672459A; WO2006/036307A2; Jul. 5, 2007. All references cited in the Search Report and not previously submitted are listed above.

* cited by examiner

*Primary Examiner* — Ula C Ruddock
*Assistant Examiner* — J. Christopher Ball
(74) *Attorney, Agent, or Firm* — Cantor Colburn LLP (57) ABSTRACT

A microfluidic device for concentrating a sample including cells or viruses and lysing the cells or viruses, the device including an anode chamber including an anode electrode, a cathode chamber including a cathode electrode and an ion exchange membrane separating the anode chamber and the cathode chamber. The cathode chamber includes a solid support therein. A method of producing the microfluidic device and a method of concentrating a sample including cells or viruses and lysing the cells or viruses therein using the microfluidic device.

25 Claims, 8 Drawing Sheets

MICROFLUIDIC DEVICE AND METHOD FOR CONCENTRATING SAMPLE CONTAINING CELLS OR VIRUSES AND LYSING CELLS OR VIRUSES, AND METHOD OF PRODUCING THE MICROFLUIDIC DEVICE

This application claims priority to Korean Patent Application No. 10-2006-0031931, filed on Apr. 7, 2006, and all the benefits accruing therefrom under 35 U.S.C. §119, the disclosure of which is incorporated herein in its entirety by reference.

BACKGROUND OF THE INVENTION

1. Field of the Invention

The present invention relates to a microfluidic device for concentrating a sample containing cells or viruses and lysing the cells or viruses, a method of producing the microfluidic device, and a method of concentrating a sample containing cells or viruses and lysing the cells or viruses using the microfluidic device.

2. Description of the Related Art

Biological analysis processes, such as the detection of pathogens and molecular diagnosis, consist of separation of target cells from a sample, concentration of a sample containing cells, separation and amplification of biomolecules from the cells, hybridization, and detection.

A lab-on-a-chip ("LOC"), which allows such a series of biological analysis processes to be rapidly and automatically performed on a microchip, is a subject that is being researched.

The LOC includes microfluidic devices in order to perform such biological analysis processes. A microfluidic device refers to a device in which inlets, outlets, reaction chambers and the like are fluidically connected through microchannels. Such microfluidic devices include, in addition to the microchannels formed thereon, micropumps for transferring a fluid, micromixers for mixing the fluid, microfilters for filtering the transferred fluid, and so on.

Conventional devices intending to integrate the biological analysis processes are composed of cell counting chambers, cell sorting chambers, deoxyribonucleic acid ("DNA") extraction chambers and polymerase chain reaction ("PCR") amplification chambers. Such chambers are sequentially and fluidically connected through channels and respectively have valves and pumps.

However, in the case of constructing a device that simply integrates the biological analysis processes, a large number of valves and microfluidic controllers are needed, thus making it difficult to integrate the biological analysis processes in a single device. A large number of chambers are also needed, thus making the volume of the device excessively large and costly. Moreover, there is a high possibility of a generation of air bubbles and a loss of samples during the transfer of sample solutions between the chambers.

Therefore, in order to miniaturize the LOC, as many biological analysis processes as possible are required to be performed in a single chamber.

BRIEF SUMMARY OF THE INVENTION

An exemplary embodiment provides a microfluidic device that allows formation of a concentrate of a sample including cells or viruses and lysis of the cells or viruses in a single chamber.

An exemplary embodiment provides a method of producing the microfluidic device.

An exemplary embodiment provides a method of simultaneously concentrating a sample including cells or viruses, and lysing the cells or viruses in a single chamber of the microfluidic device.

In an exemplary embodiment, there is provided a microfluidic device for concentrating a sample including cells or viruses and lysing the cells or viruses. The device includes an anode chamber including an anode electrode, a cathode chamber including a cathode electrode and an ion exchange membrane separating the anode chamber and the cathode chamber. The cathode chamber includes a solid support.

In an exemplary embodiment, a surface of the solid support is coated with a cell-binding substance.

In an exemplary embodiment, the cell-binding substance is a hydrophobic substance having a water contact angle of about 70° to about 90° or a charge donor substance.

In an exemplary embodiment, the hydrophobic substance is selected from the group consisting of octadecyltrichlorosilane (OTS), tridecafluorotetrahydrooctyl trimethoxysilane (DTS), octadecyidimethyl(3-trimethoxysilyipropyl)ammonium chloride (OTC), polyethyleneiminetrimethoxysilane (PEIM), and mixtures thereof.

In an exemplary embodiment, the solid support has a structure selected from the group consisting of a flat structure, a pillar structure, a bead structure and a sieve structure.

In an exemplary embodiment, the ion exchange membrane conducts electric current but does not allow permeation of ions and gases that are generated by electrolysis in the anode chamber and the cathode chamber.

In an exemplary embodiment, the cathode electrode includes a metal which is able to absorb hydrogen gas. The anode electrode includes a metal which has a higher standard oxidation potential than that of water and does not react with water.

In an exemplary embodiment, the cathode electrode is formed of palladium (Pd).

In an exemplary embodiment, the anode electrode is formed of a metal selected from the group consisting of copper (Cu), lead (Pb), silver (Ag), chromium (Cr), titanium (Ti), nickel (Ni), zinc (Zn), iron (Fe), and tin (Sn).

In an exemplary embodiment, the cathode chamber and the anode chamber, respectively, further include an inlet and an outlet for introduction and discharge of a solution.

In an exemplary embodiment, the microfluidic device for concentrating a sample including cells or viruses and lysing the cells or viruses may further a first adhesive layer formed on a first side of the ion exchange membrane, a second adhesive layer formed on a second side of the ion exchange membrane opposing the first side, an anode electrode supporting substrate that is adhered to the first adhesive layer and has a ladder-shaped opening, the anode electrode fixed on the anode electrode supporting substrate and corresponding in shape with the ladder shape of the opening of the anode electrode supporting substrate, an anode chamber substrate that forms the anode chamber while covering the anode, a cathode chamber substrate that is adhered to the second adhesive layer, forming the cathode chamber and including the solid support having its upper surface adhered to the second adhesive layer and the cathode electrode fixed on a bottom of the cathode chamber.

In an exemplary embodiment, the first adhesive layer and the second adhesive layer may respectively have sufficient adhesive power and may be thin enough to conduct electric current.

In an exemplary embodiment, the anode electrode supporting substrate may be formed of a printed circuit board ("PCB").

In an exemplary embodiment, there is provided a method of producing a microfluidic device for concentration of a sample including cells or viruses and lysis of the cells or viruses. The method includes producing an anode electrode supporting substrate including a ladder-shaped anode electrode on a side and an opening corresponding in shape with the ladder-shaped anode electrode, fixing an anode chamber substrate on the anode electrode supporting substrate and forming an anode chamber while covering the anode electrode, producing a cathode chamber substrate including a solid support, forming a cathode chamber, and including a cathode electrode fixed on a bottom of the cathode chamber, forming a first adhesive layer and a second adhesive layer on respective sides of an ion exchange membrane, adhering the anode electrode supporting substrate to the first adhesive layer and adhering the cathode chamber substrate to the second adhesive layer.

In an exemplary embodiment, the production an anode electrode supporting substrate may include coating a photoresist film on a metal-coated printed circuit board (PCB), irradiating ultraviolet ("UV") light through a mask having a pattern designed to form the ladder-shaped anode electrode, and developing the pattern on the anode electrode exposing the metal coated PCB, etching the exposed metal coated PCB and cutting the exposed PCB to form then opening.

In an exemplary embodiment, the producing a cathode chamber substrate may include coating a photoresist film on a solid substrate, irradiating UV light through a mask having a pattern designed to form the solid support, and developing the pattern and exposing the solid substrate, etching the exposed solid substrate, vapor depositing a metal on the solid substrate by vacuum evaporation involving heating with an electron beam, removing the photoresist film and electroplating the metal-deposited side of the solid substrate with another metal.

In an exemplary embodiment, the producing a cathode chamber substrate may further include coating the surface of the solid support with a cell-binding substance.

In an exemplary embodiment, the forming adhesive layers may include spin coating an adhesive on opposing sides of the ion exchange membrane, adhering one side of the ion exchange membrane on the anode electrode supporting substrate while spreading the ion exchange membrane with a roller, and bonding the other side of the ion exchange membrane to the cathode chamber substrate.

In an exemplary embodiment, the adhesive may be liquid at ambient temperature and may attain adhesiveness while being cured, when heat or ultraviolet light is applied.

In an exemplary embodiment, the adhesion of the adhesive layers to the electrode supporting substrates may include arranging the anode electrode supporting substrate, the ion exchange membrane and the cathode chamber substrate in an array and applying heat and pressure.

In an exemplary embodiment, there is provided a method of concentrating a sample including cells or viruses and lysing the cells or viruses using a microfluidic device. The method includes introducing a solution which includes a species of ion with a standard oxidation potential higher or lower than that of water into the anode chamber of the microfluidic device, introducing a solution which includes a species of ion with a standard reduction potential lower than that of cells or viruses and that of water into the cathode chamber of the microfluidic device and applying electric current through the anode electrode and the cathode electrode inducing electrolysis in the anode chamber and the cathode chamber adjusting pH of the solution introduced into the anode chamber or the cathode chamber.

In an exemplary embodiment, the ions that are introduced into the anode chamber and have a lower standard oxidation potential lower than that of water include at least one selected from the group consisting of $NO_3^-$, $F^-$, $SO_4^{2-}$, $PO_4^{3-}$ and $CO_3^{2-}$.

In an exemplary embodiment, the ions that are introduced into the anode chamber and have a standard oxidation potential higher than that of water include $Cl^-$.

In an exemplary embodiment, the ions that are introduced into the cathode chamber and have a lower standard oxidation potential lower than that of water include at least one selected from the group consisting of $Na^+$, $K^+$, $Ca^{2+}$, $Mg^{2+}$ and $Al^{3+}$.

In an exemplary embodiment, the pH of the solution may be adjusted by varying the direction of the applied electric current, the intensity of the applied electric current, the duration of electric current application, the width of the electrode, or the thickness of the ion exchange membrane.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the size and relative sizes of layers and regions may be exaggerated for clarity.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "lower", "above", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "above" the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Hereinafter, the present invention will be described in detail with reference to the accompanying drawings.

Figure 1:
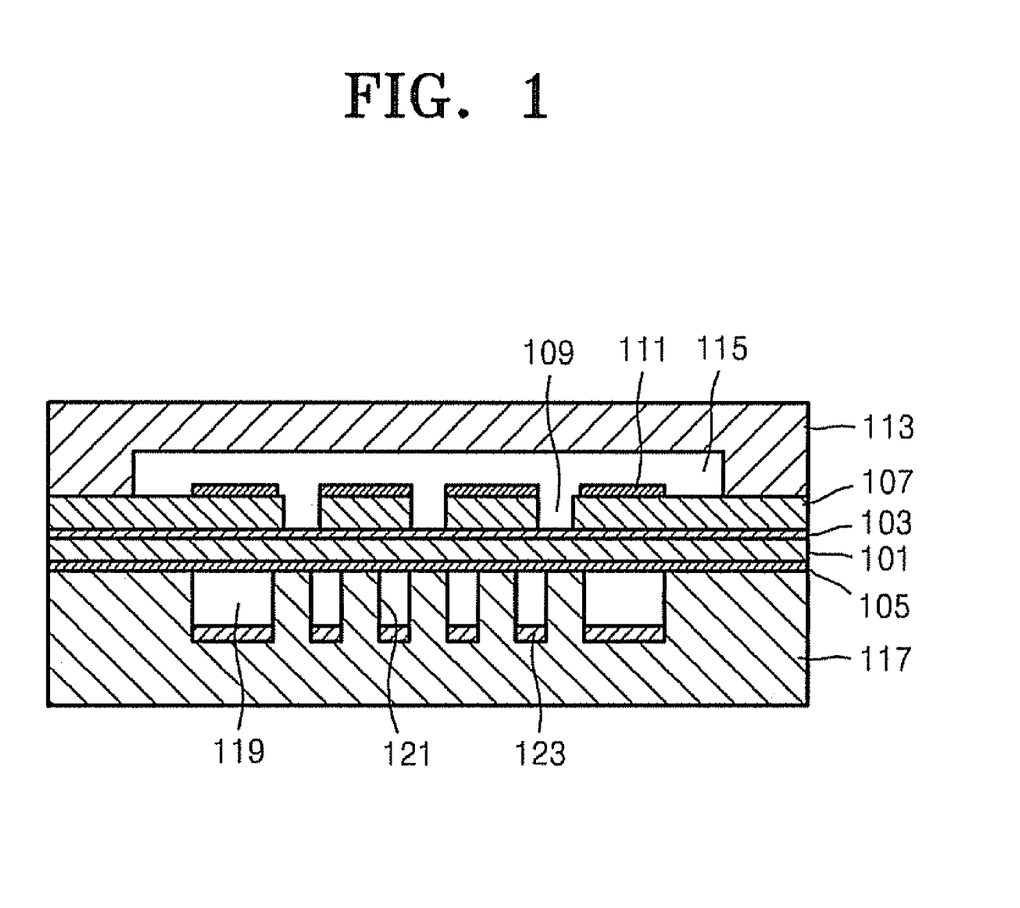
FIG. 1 illustrates a lateral cross-sectional view of an exemplary embodiment of a microfluidic device according to the present invention.

FIG. 1 is a lateral cross-sectional view of an exemplary embodiment of a microfluidic device according to the present invention.

Referring to FIG. 1, the microfluidic device includes an ion exchange membrane 101, a first adhesive layer 103, a second adhesive layer 105, an anode electrode supporting substrate 107, an anode electrode 111, an anode chamber substrate 113, a cathode chamber substrate 117, and a cathode electrode 123.

The ion exchange membrane 101 conducts electric current but does not allow permeation of ions or gases generated by electrolysis in an anode chamber and a cathode chamber. In one exemplary embodiment, the ion exchange membrane 101 conducts electric current but does not allow permeation of protons and hydroxide ions in the anode chamber and the cathode chamber.

In exemplary embodiments, the ion exchange membrane 101 may be a cation exchange membrane or an anion exchange membrane. The cation exchange membrane is a membrane that allows cations to permeate through but shows an approximate 100% resistance to the permeation of anions. Alternatively, the anion exchange membrane is a membrane that allows anions to permeate through but shows an approximate 100% resistance to the permeation of cations.

In an exemplary embodiment, the cation exchange membrane may be a relatively strong acid exchange membrane (including —$SO_3$—; Nafion™), or a relatively weak acid exchange membrane (including —COO—). The anion exchange membrane may be a relatively strong base exchange membrane (including $N^+$ ($CH_3$)) or a relatively weak base exchange membrane (including $N(CH_3)_2$).

Any of a number of cation exchange membranes and anion exchange membranes may be suitable for the purposes described herein. In exemplary embodiments, the ion exchange membrane 101 is commercially available under the trade names of Nafion™ (Dupont Corp.), Dowex™ (Sigma-Aldrich Co.), and Diaion™ (Sigma-Aldrich Co.).

The first adhesive layer 103 is formed on a side (e.g., an upper surface) of the ion exchange membrane 101. The second adhesive layer 105 is formed on another side of the ion exchange membrane 101 opposite to the first adhesive layer 103 (e.g., a lower surface of the ion exchange membrane 101). The first adhesive layer 103 and the second adhesive layer 105 have sufficient adhesive power and also are relatively thin enough to conduct electric current.

In an exemplary embodiment, the first adhesive layer 103 and the second adhesive layer 105 may be respectively formed by coating an adhesive, which is liquid at ambient temperature and attains adhesiveness while being cured when heat is applied, on both sides of the ion exchange membrane 101, and heating the adhesive layers. In the illustrated embodiment of the present invention, Dow Corning Primer 1205 was used as the adhesive.

The anode electrode supporting substrate 107 is adhered to the first adhesive layer 103 (e.g., above the ion exchange member 101) and includes a ladder-shaped opening 109. In exemplary embodiments, the anode electrode supporting substrate 107 may be formed of a substance selected from the group consisting of a printed circuit board ("PCB"), silicon wafer, glass, quartz, metals and plastics. In one exemplary embodiment, the anode electrode supporting substrate 107 may be formed of a PCB.

In an exemplary embodiment when the PCB is used as the anode electrode supporting substrate 107, processing is facilitated and a width of an opening through which electric current is conducted can decrease, so that the number of electrodes in a single transverse row can be increased. Advantageously, the electrical resistance can be decreased, the pH change distribution can be uniformly controlled and the effects of a pillar-structured chip can be maximized. Additionally, the price of mass production of the microfluidic device can decrease. For instance, the method of forming the opening on a PCB can be achieved at a price that is about one hundred times cheaper than the method of forming an opening on a glass substrate by sand blasting.

The anode electrode 111 is fixed on the anode electrode supporting substrate 107 (e.g. on an upper surface) The anode electrode 111 may be shaped in accordance with the ladder-shaped opening 109 of the anode electrode supporting substrate 107. The anode electrode 111 may be formed of a metal that has a higher standard oxidation potential than that of water and does not react with water. In the illustrated embodiment, gases are not generated in an anode chamber 115, and thus, the anode chamber 115 does not need to have a gas outlet.

The anode electrode 111 may be formed of a metal selected from metals that have higher oxidation potentials than that of water and do not react with water, but the anode electrode 111 is not limited thereto.

In the electrolysis of water, oxygen gas is generated in the vicinity of the anode electrode 111 to generate foams and protons are generated to lower the pH of the solution. In contrast, the microfluidic device of the illustrated embodiment employs a metal having a higher standard oxidation potential than that of water, so that the metal is oxidized and ionized, without water being electrolyzed and without gas being generated. Furthermore in the microfluidic device of the illustrated embodiment, a small amount of oxygen that may be generated under certain conditions such as an increase in the voltage and change in the solute, binds to the metal having a higher standard oxidation potential than that of water, to form a metal oxide, and thereby, foaming due to generation of oxygen gas does not occur.

The metal that has a higher standard oxidation potential than that of water but reacts with water may not be suitable to be used as the anode electrode 111 of the illustrated embodiment. Metals such as potassium (K), calcium (Ca), sodium (Na) and magnesium (Mg) may not suitable to be used as the anode electrode 111.

Furthermore, a metal that has a higher standard oxidation potential than that of water but forms an oxidized film too quickly, thereby causing the resistance to increase, may also not be suitable to be used as the anode electrode 111 of the illustrated embodiment. Metals such as aluminum (Al) is rapidly oxidized to alumina, and thus may not be suitable to be used as the anode electrode 111.

The anode electrode 111 of the illustrated embodiment may be formed of a metal selected from the group consisting of copper (Cu), lead (Pb), silver (Ag), chromium (Cr), titanium (Ti), nickel (Ni), zinc (Zn), iron (Fe) and tin (Sn).

Referring again to FIG. 1, the anode chamber substrate 113 covers the anode electrode 111 and forms the anode chamber 115. An upper portion of the anode chamber substrate 113 is separated from the anode electrode 113 and the anode electrode supporting substrate 107 forming the anode chamber 115.

The cathode chamber substrate 117 is adhered to the second adhesive layer 105 (e.g., on portions of the lower surface of the second adhesive layer 105). The cathode chamber substrate 117 forms a cathode chamber 119 at remaining portions at the lower surface of the second adhesive layer 105 where the cathode chamber substrate 117 is not adhered. The cathode chamber substrate 117 includes a plurality of pillars 121 which include upper faces of the pillars 121 adhered to the portions of the second adhesive layer 105.

In exemplary embodiments, the pillars 121 may have a structure selected from a flat structure, a pillar structure, a bead structure and a sieve structure.

The pillars 121 may be configured or formed such that cells can bind thereto. In one exemplary embodiment, the binding of the cells to the pillars 121 can be achieved through physical or chemical properties, such as hydrophobicity and/or charge, of the surface of the pillars 121. In exemplary embodiments the pillars 121 have a cell-binding substance coated on a surface of the pillars 121. The cell-binding substance is not particularly limited, so long as the cell-binding substance is a substance capable of providing hydrophobicity or charge to the pillars 121 and capable of capturing cells or viruses. In one exemplary embodiment, the cell-binding substance may be a hydrophobic substance having a water contact angle of about 70° to about 90° or a charge donor substance.

A representative method of determining the degree of hydrophobicity of the surface of the pillars 121 utilizes the water contact angle. As the water contact angle of the surface of the pillars 121 increases, the degree of hydrophobicity increases. In exemplary embodiments, when a solution including cells or viruses is contacted with a hydrophobic pillars 121 having a water contact angle of 70° to 90°, the cells or viruses bind to the pillars 121 through hydrophobic interaction with the hydrophobic pillars 121, or the like. The hydrophilic pillars 121 hardly bind with the cells or viruses, as shown in the following Examples. Furthermore, when the water contact angle of the hydrophobic pillars 121 is less or higher than the aforementioned range, the quantity of cells or viruses binding to the hydrophobic pillars 121 may decrease.

The hydrophobic substance may include, but is not limited to, octadecyltrichlorosilane ("OTS"), tridecafluorotetrahydrooctyl trimethoxysilane ("DTS"), octadecyldimethyl(3-trimethoxysilylpropyl)ammonium chloride ("OTC"), polyethyleneiminetrimethoxysilane ("PEIM"), and the like.

The cathode electrode 123 is fixed on a bottom of the cathode chamber 119 but is not fixed on the pillars 121. The cathode electrode 123 may be formed of a metal that can adsorb hydrogen gas. In the illustrated embodiment, since no gases are generated in the cathode chamber 119, the cathode chamber 119 does not need to have a gas outlet.

The cathode electrode 123 may be formed of a metal selected from any metal that can absorb hydrogen gas, but the cathode electrode is not particularly limited thereto. In one exemplary embodiment, the cathode electrode 123 may be formed of palladium (Pd) that is known to have an ability to absorb a large quantity of hydrogen gas (See Bhadra Munasiri, et al., J. Electroanal. Chem., pp 333-337, 1992). In using Pd for the cathode electrode 123, Pd can reduce or effectively prevent the generation of gases by adsorbing to hydrogen gas that is generated in the vicinity of the cathode electrode 123 due to the electrolysis of water. The OH— ions which are generated simultaneously with the electrolysis of water, can raise the pH of the solution in the vicinity of the cathode electrode 123.

Figure 2:
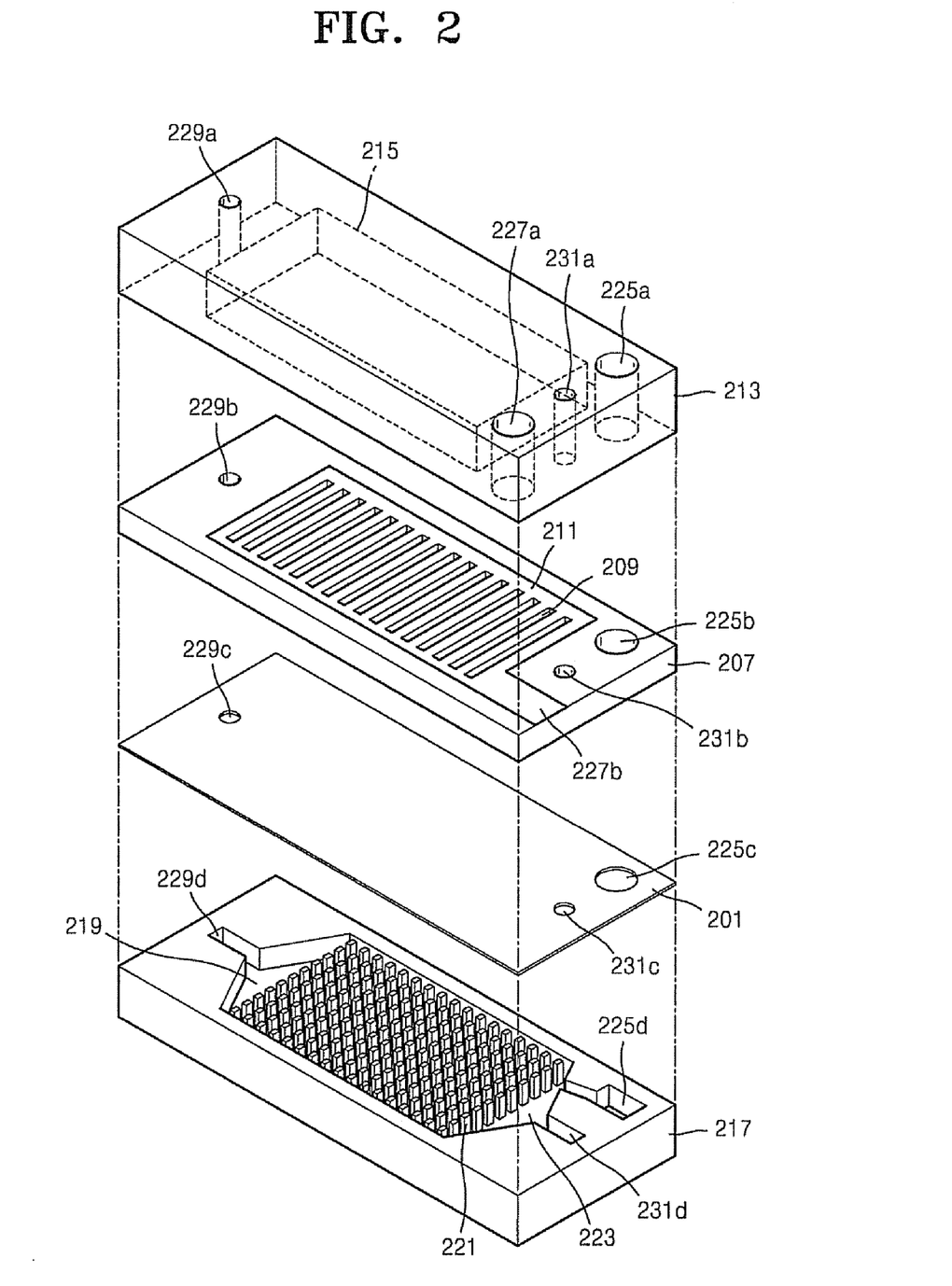
FIG. 2 illustrates an exploded perspective view of an exemplary embodiment of a microfluidic device according to the present invention.

FIG. 2 is an exploded perspective view of a microfluidic device according to the present invention.

Referring to FIG. 2, the microfluidic device includes an anode chamber substrate 213, an anode electrode supporting substrate 207, an ion exchange membrane 201 and a cathode chamber substrate 217.

The anode chamber substrate 213 includes a space for forming an anode chamber 215, an inlet 229a, an outlet 231a, a cathode electrode hole 225a, and an anode electrode hole 227a.

The anode electrode supporting substrate 207 includes a substantially ladder-shaped opening 209, an anode electrode 211 corresponding in shape with the ladder-shaped opening 209, an inlet 229b, an outlet 231b, a cathode electrode hole 225b and an anode electrode pad 227b.

The ion exchange membrane 201 includes an inlet 229c, an outlet 231c, and a cathode electrode hole 225c.

The cathode chamber substrate 217 includes a cathode chamber 219, a plurality of pillars 221, a cathode electrode 223 fixed on a bottom of the cathode chamber 219, an inlet 229d, an outlet 231d and a cathode electrode pad 225d.

The inlets 229a, 229b, 229c and 229d are aligned (e.g. positionally in a vertical direction) together, and the outlets 231a, 231b, 231c and 231d are also aligned together. Furthermore, the cathode electrode holes 225a, 225b and 225c, and the cathode electrode pad 225d are also aligned together, and the anode electrode hole 227a and the anode electrode pad 227b are also aligned together.

Figure 3A:
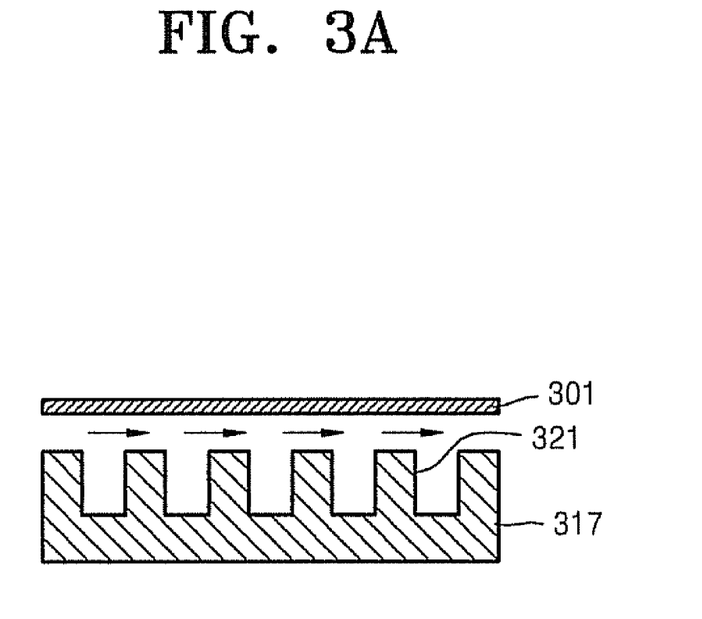
FIG. 3A is a diagram illustrating an exemplary embodiment of a phenomenon where upper faces of pillars in a microfluidic device according to the present invention are not completely bonded to an ion exchange membrane and a flowing solution flows over the upper faces of the pillars.

FIG. 3A is a diagram illustrating an exemplary embodiment of a phenomenon where upper faces of the pillars 321 in a microfluidic device are not completely bonded to the ion exchange membrane 301 and a flowing solution flows over the upper faces of the pillars, e.g., between the ion exchange membrane 301 and the pillars 321 of a cathode chamber substrate 317 as illustrated by the arrows. Referring to FIG. 3A, a solution including cells or viruses completely flows over the upper faces of the pillars 321. The cells or viruses cannot be captured by the pillars 321, and thus, the concentration of the solution including the cells or viruses cannot be achieved.

Figure 3B:
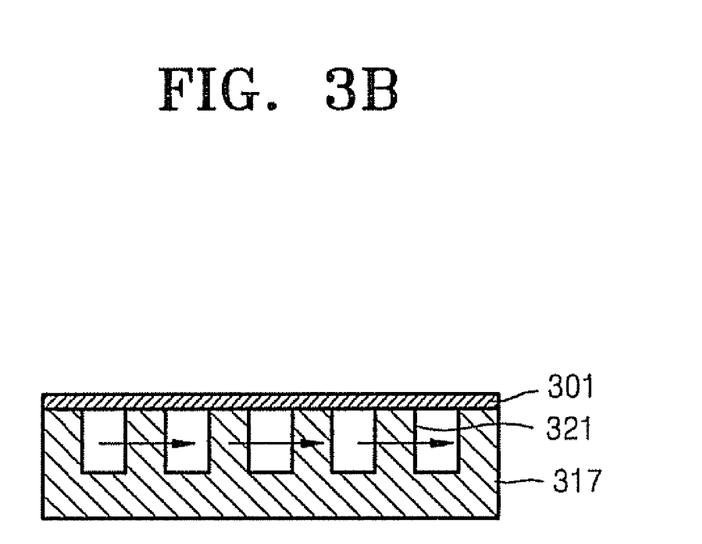
FIG. 3B is a diagram illustrating an exemplary embodiment of a phenomenon where the lateral surfaces of the pillars are completely bonded to an ion exchange membrane in a microfluidic device according to the present invention and a flowing solution flows through the lateral sides of pillars.

FIG. 3B is a diagram illustrating an exemplary embodiment of a phenomenon where the upper faces of pillars 321 in a microfluidic device are bonded (e.g., completely without a gap) to an ion exchange membrane 301 and a flowing solution flows through lateral sides of the pillars 321 as illustrated by the arrows. Referring to FIG. 3B, unlike the case illustrated in FIG. 3A, when a solution including cells or viruses flows through the pillars 321, the cells or viruses can be captured by the pillars 321, and thus, a concentration of the solution including the cells or viruses can be achieved. The microfluidic device of the illustrated embodiments achieving the concentration of a solution including cells or viruses by introducing a first adhesive layer and a second adhesive layer.

In the microfluidic device of the illustrated embodiments, the anode chamber and the cathode chamber refer to spaces that can hold a substance such as a fluid. In exemplary embodiments, the anode chamber and/or the cathode chamber may be microchambers which can hold a substance to a volume of sub-microliters, but the microchambers are not limited thereto.

The microfluidic device according to the illustrated embodiments is not particularly limited in the specific form, structure, size and the like described hereinabove.

The cathode chamber and/or the anode chamber of a microfluidic device may respectively further include an inlet and outlet for introduction and discharge of a solution, and may further include a micropump for receiving and discharging of the solution.

In the illustrated embodiments of the microfluidic device, a solution including ions which have a standard oxidation potential higher or lower than that of water, namely, an electrolyte to be electrolyzed, can be introduced into the anode chamber. The ions having a lower standard oxidation potential than that of water may include, but are not limited to, at least one type of ion including anions such as $NO_3^-$, $F^-$, $SO_4^{2-}$, $PO_4^{3-}$ and $CO_3^{2-}$ The ions having a higher standard oxidation potential than that of water may be provided by an electrolyte including $Cl^-$ ions, but the present invention is not limited to thereto.

In an exemplary embodiment, when the solution introduced into the anode chamber includes a compound having a lower standard oxidation potential than that of water and when electrolysis is performed using the microfluidic device of the illustrated embodiment, water is electrolyzed in the anode chamber to generate oxygen gas and $H^+$ ions. The pH of the solution in the anode chamber decreases due to the presence of the $H^+$ ions.

In an alternative embodiment, when a metal, which has a higher standard oxidation potential than that of water and does not react with water, is used as the anode electrode, the metal having a higher standard oxidation potential than that of water is oxidized, and oxygen gas is not generated. The Cl⁻ ions having a higher standard oxidation potential than that of water may be particularly used for the purpose of cell lysis.

In the microfluidic device of the illustrated embodiments, a solution including cells or viruses and ions having a lower standard oxidation potential than that of water can be introduced into the cathode chamber. The ions include $Na^+$, $K^+$, $Ca^{2+}$, $Mg^{2+}$, $Al^{3+}$ and the like, but are not limited thereto. Therefore, in the case of performing electrolysis using a microfluidic device according of the illustrated embodiments, water is electrolyzed in the cathode chamber to generate hydrogen gas and OH⁻ ions. The solution in the cathode chamber attains a higher pH due to the presence of the OH⁻ ions.

When a metal, which can adsorb hydrogen gas, is used as the cathode electrode, the hydrogen gas thus generated is adsorbed, and no gas bubbles are generated.

In the exemplary embodiments, the cells or viruses may include bacterial cells, bacteriophages, plant cells, animal cells, plant viruses, animal viruses and the like, but the specific type of cells or viruses is not particularly limited thereto.

Figure 4:
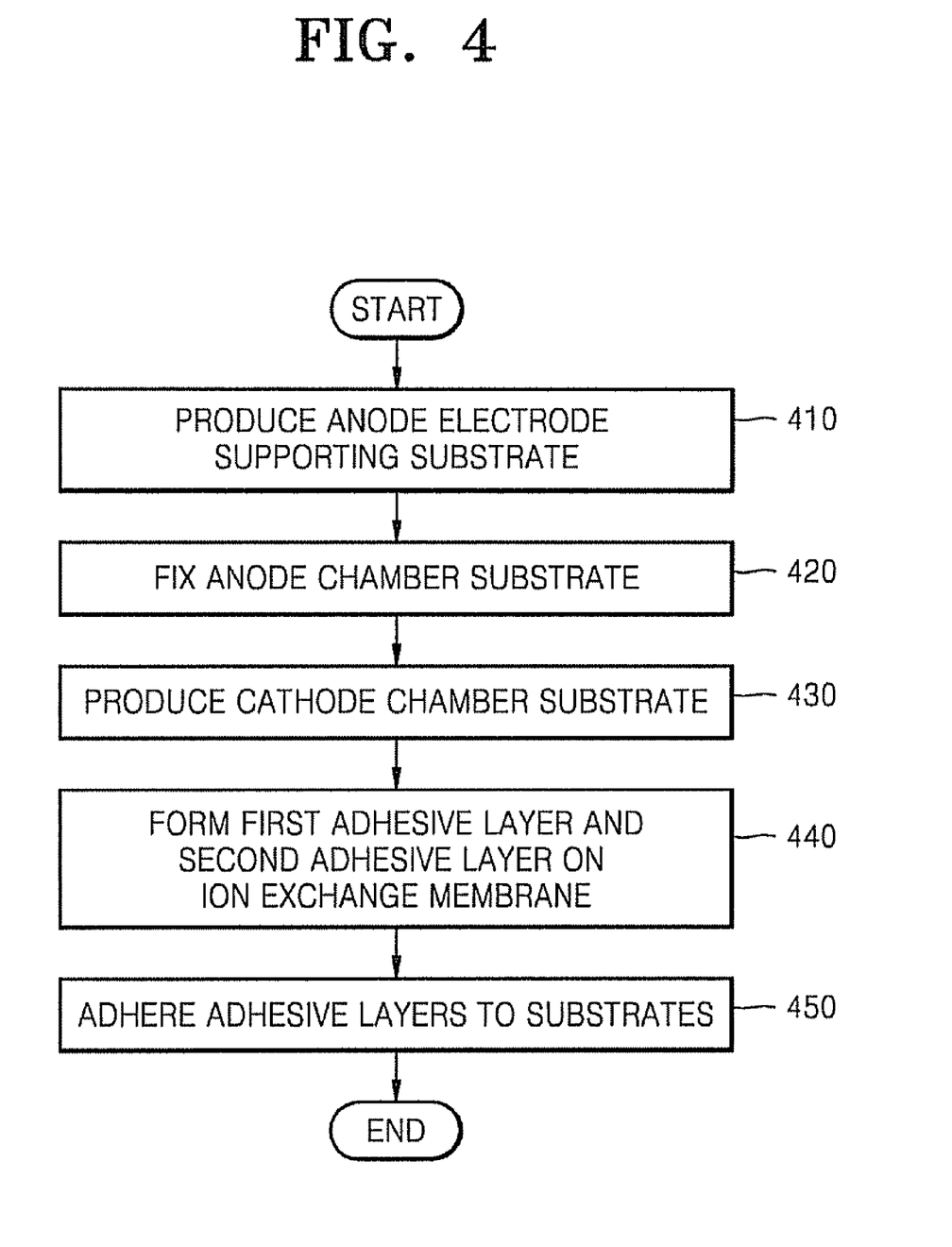
FIG. 4 is a flow diagram illustrating an exemplary embodiment of a method of producing a microfluidic device according to the present invention.

FIG. 4 is a flow diagram illustrating an exemplary embodiment of a method of producing a microfluidic device according to the present invention.

Referring to FIG. 4, an anode electrode supporting substrate, which includes a ladder-shaped anode electrode and an opening corresponding in shape with the ladder shape of the anode electrode, is produced (410).

Figure 5:
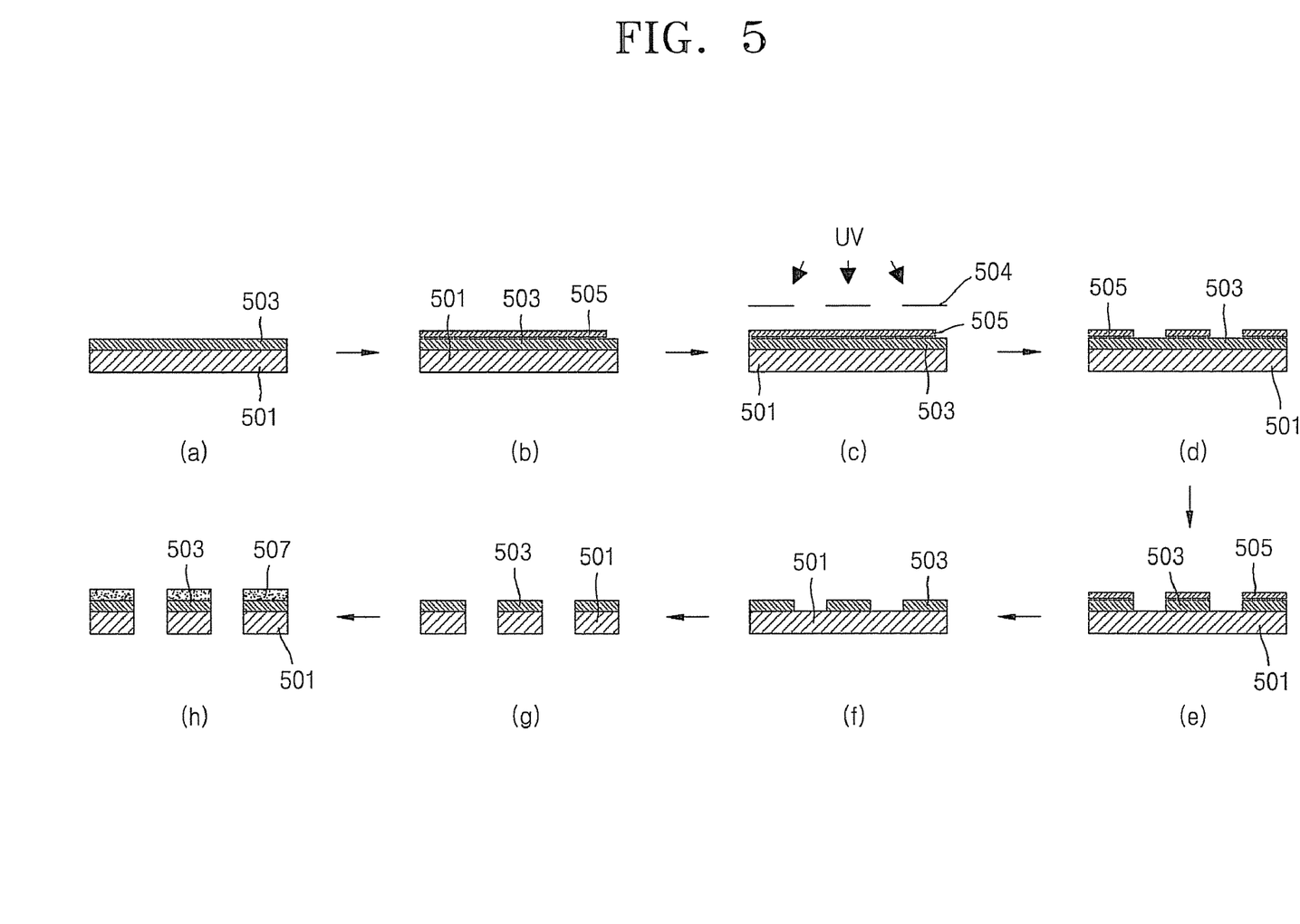
FIG. 5 is a diagram illustrating an exemplary embodiment of a process of producing an anode electrode supporting substrate of a microfluidic device according to the present invention.

FIG. 5 is a schematic diagram illustrating an exemplary embodiment of a process of producing an anode electrode supporting substrate of a microfluidic device according to the present invention.

Referring to FIG. 5, to produce the anode electrode supporting substrate, a photoresist film 505 is coated on a PCB 501 (FIG. 5*a*), which has been coated with a metal 503 in advance (FIG. 5*b*). Ultraviolet ("UV") light is irradiated (as shown by the arrows) through a mask 504 having a pattern designed to form a ladder-shaped anode electrode in order to expose the photoresist film 505 to the UV light (FIG. 5*c*). The pattern is developed (FIG. 5*d*). The exposed metal 503 is etched (FIG. 5*e*) and the photoresist film 505 is peeled off (FIG. 5*f*). The exposed PCB 501 is etched to form an opening (FIG. 5*g*) and another metal 507 is coated on the remaining metal 503 (FIG. 5*h*).

Referring again to FIG. 4, an anode chamber substrate is fixed on the anode electrode supporting substrate, thereby forming an anode chamber to cover the anode electrode (420).

A cathode chamber substrate that includes a solid support, such as a plurality of pillars, forms a cathode chamber, and includes a cathode electrode that is fixed on the cathode chamber (430).

Figure 6:
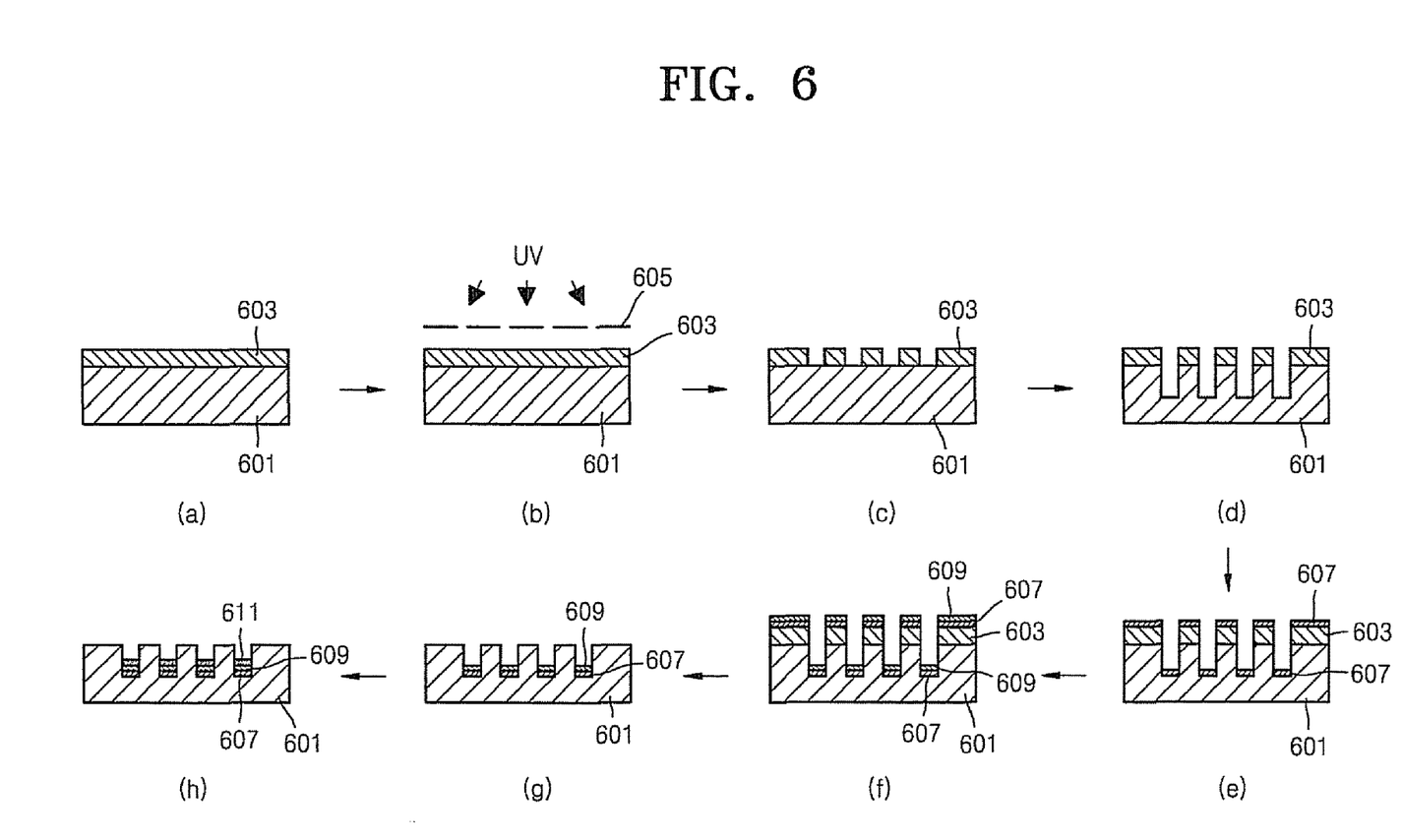
FIG. 6 is a diagram illustrating an exemplary embodiment of a process of producing a cathode chamber substrate of a microfluidic device according to the present invention.

FIG. 6 is a schematic diagram illustrating an exemplary embodiment of a process of producing a cathode chamber substrate of a microfluidic device according to the present invention.

Referring to FIG. 6, in order to produce the cathode chamber substrate, a photoresist film 603 is first coated on a silicon wafer 601 (FIG. 6*a*), UV light (as shown by the arrows) is irradiated through a mask 605 having a pattern designed to form pillars (FIG. 6*b*) and the pattern is developed on the mask 605 (FIG. 6*c*). The exposed silicon wafer 601 is etched and metals 607 and 609 are sequentially vapor deposited on the silicon wafer 601 by vacuum evaporation involving heat with an electron beam (FIGS. 6*e* and 6*f*). The photoresist film 603 is removed using a solvent (at this time, the metal 607 on the photoresist film 603 is removed as well) (FIG. 6*g*) and another metal 611 is electroplated on the metal 609 on the silicon wafer 601 (FIG. 6*h*). The production of the cathode chamber substrate may further include coating a cell-binding substance on the surfaces of the formed pillars (not shown).

Referring to FIG. 4 again, a first adhesive layer and a second adhesive layer are then formed on the respective sides of an ion exchange membrane (440).

In exemplary embodiments, a formation of the first and second adhesive layers may include spin coating an adhesive on both sides of the ion exchange membrane, adhering one side of the ion exchange membrane to the anode electrode supporting substrate while spreading the ion exchange membrane with a roller, and bonding the other side of the ion exchange membrane to the cathode chamber substrate.

In an exemplary embodiment, the adhesive may be liquid at ambient temperature and may attain adhesiveness while being cured, such as when heat or ultraviolet light is applied. In the illustrated embodiments, Dow Corning Primer 1205 was used as the adhesive.

The anode electrode supporting substrate adheres to the first adhesive layer and the cathode chamber substrate adheres to the second adhesive layer (450). In an exemplary embodiment, the adhesion of the first and second adhesive layers and the anode electrode supporting and cathode chamber substrates, respectively, may be performed by arranging the anode electrode supporting substrate, the ion exchange membrane and the cathode chamber substrate in an array, and thereto applying heat and pressure.

An exemplary embodiment provides a method of concentrating a sample including cells or viruses and lysing the cells or viruses using a microfluidic device according to the present invention. The method of concentrating a sample including cells or viruses and lysing the cells or viruses using the microfluidic device includes introducing a solution, which includes ions having a standard oxidation potential higher or lower than that of water into the anode chamber of the microfluidic device.

A solution including cells or viruses and ions having a lower standard reduction potential than that of water is introduced into the cathode chamber of the microfluidic device. Electric current is applied through the anode electrode and the cathode electrode in order to induce electrolysis in the anode chamber and the cathode chamber, and to adjust the pH of the solution introduced into the anode chamber or the cathode chamber.

Exemplary embodiments of an anion having a lower standard oxidation potential than that of water, an anion having a higher standard oxidation potential than that of water and a cation having a lower standard reduction potential than that of water and examples of cells or viruses are respectively described above. However, introducing a solution including ions having a standard oxidation potential higher or lower than that of water into the anode chamber and introducing a solution including cells or viruses and ions having a lower standard reduction potential than that of water into the cathode chamber may be performed substantially simultaneously or sequentially.

The pH of the solutions can be adjusted by varying the direction of the applied electric current, the intensity of the applied electric current, the duration of the applied electric current, the width of the electrode and/or the thickness of the ion exchange membrane. Relatively precise values of the direction of the applied electric current, the intensity of the applied electric current, the duration of the applied electric current, the width of the electrode and the thickness of the ion exchange membrane may vary according to the desired pH, the volume of the chamber, or the like.

When a sample solution including NaCl is introduced into the anode and the cathode, and then electrolyzed, chloride ions, not water, are electrolyzed to generate chlorine gas in the anode chamber. Protons are generated in a smaller amount than that of hydroxide ions that are generated in the cathode chamber. This amount of protons results from a reaction of chlorine gas with water, and varies according to the conditions for dissolving of the chlorine gas, thus making it difficult to control the pH of the sample solution.

In order to address these issues, the illustrated embodiments use a compound having a standard oxidation potential lower than that of water and a compound having a standard reduction potential lower than that of water in the anode chamber and the cathode chamber, respectively. However, in the case of only lysing cells, a sample solution including NaCl can be introduced to the anode electrode and the cathode electrode, and then electrolyzed, so that the cells can be lysed at the cathode electrode.

As in the illustrated embodiments, since a solution for cathode chamber, which includes a compound having a lower standard reduction potential than that of water, is introduced into the cathode chamber, water is electrolyzed in the cathode chamber in order to generate hydrogen gas and $OH^-$ ions. Moreover, since a solution for the anode chamber, which includes a compound having a lower standard reduction potential than that of water, is introduced into the anode chamber, water is electrolyzed in the anode chamber in order to generate oxygen gas and $H^+$ ions. As a result, the solution in the cathode chamber is basic in terms of pH, while the solution in the anode chamber is acidic in terms of pH.

Alternatively, as discussed above, when a metal having a higher standard oxidation potential than that of water and that does not react with water is used as the anode electrode, and a metal that can adsorb hydrogen gas is used as the cathode electrode, a gas generation in the anode chamber and the cathode chamber can be reduced or effectively prevented.

Hereinafter, the present invention will be described in detail with reference to the following Examples. However, these Examples are for illustrative purposes only, and the scope of the present invention is not intended to be limited by the Examples.

EXAMPLE 1

Production of Microfluidic Device

An anode chamber substrate as illustrated in FIG. 2 was produced using a silicon wafer.

An anode electrode supporting substrate was produced using the method illustrated in FIG. 5. A PCB was used as the anode electrode supporting substrate, and lead was coated thereon for an anode electrode. The breadth and length of the anode electrode supporting substrate were about 14 mm and about 34 mm, respectively, the width of the opening was about 1.0 mm, and the width of a transverse unit electrode was about 0.5 mm.

Figure 7A:
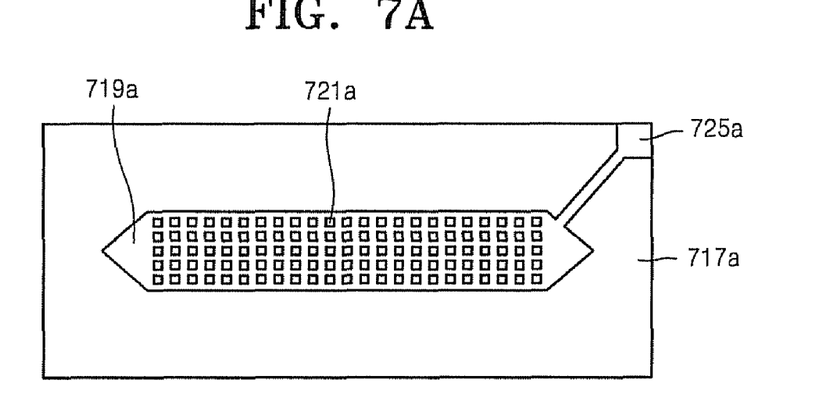
FIG. 7A to FIG. 7C are diagrams respectively illustrating exemplary embodiments of differently shaped upper sides of cathode chamber substrates produced in the Examples of the present invention.

A cathode chamber substrate was produced using the method illustrated in FIG. 6. The silicon wafer was used as the substrate, and palladium was coated thereon for the cathode electrode. FIG. 7A is a diagram illustrating an exemplary embodiment of an upper surface of a cathode chamber substrate 717a produced in the present invention. Referring to FIG. 7A, a plurality of pillars 721a are formed on the cathode chamber substrate 717a, a cathode electrode 719a is formed on a bottom of the cathode chamber in addition to the pillars 721a, and a cathode electrode pad 725a that may be connected to a power supply (not shown) is provided.

Dow Corning Primer 1205 was spin coated (500 revolutions per minute ("rpm"), 5 seconds (s); 700 rpm, 10 s) on the silicon wafer as an adhesive, a cation exchange membrane containing —$SO_3$—$Na^+$ group is bonded on the silicon wafer using a roller, and then Dow Corning Primer 1205 was spin coated thereon (500 rpm, 5 s; 1500 rpm, 10 s) to form a first adhesive layer and a second adhesive layer on the cation exchange membrane. The Dow Corning Primer 1205 includes a low viscosity, such as water does, at room temperature and has no adhesiveness. However, when heat is applied to the Dow Corning Primer 1205, the adhesive is solidified and obtains adhesiveness.

The anode chamber substrate, the anode electrode supporting substrate, the cation exchange membrane, and the cathode chamber substrate produced as described above were arranged in an array, and were bonded together by heating to a temperature of about 120° C. and applying a pressure of about 1 ton for 30 minutes in order to produce the microfluidic device of the illustrated embodiments. The volumes of the produced cathode chamber and anode chamber were respectively 10 microliters (µl).

EXAMPLES 2 to 6

Production of Microfluidic Device

Microfluidic devices of Examples 2 through 6 were produced in the same manner as in Example 1, except that the shape of the cathode chamber substrate differed.

Figure 7B:
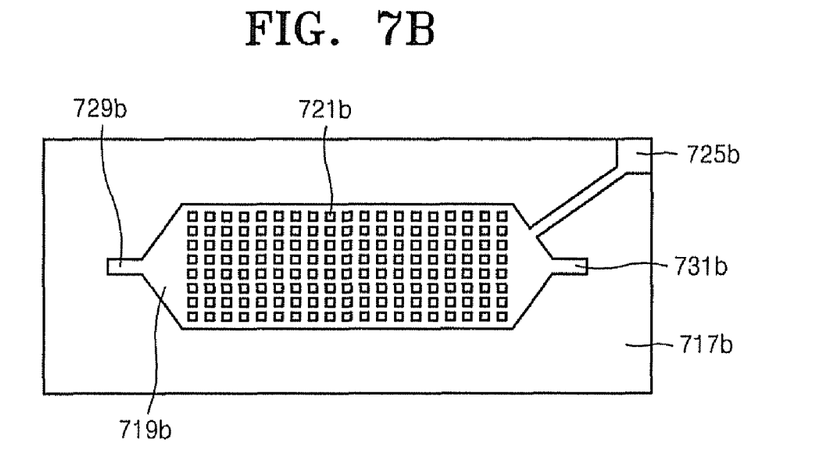
Figure 7C:
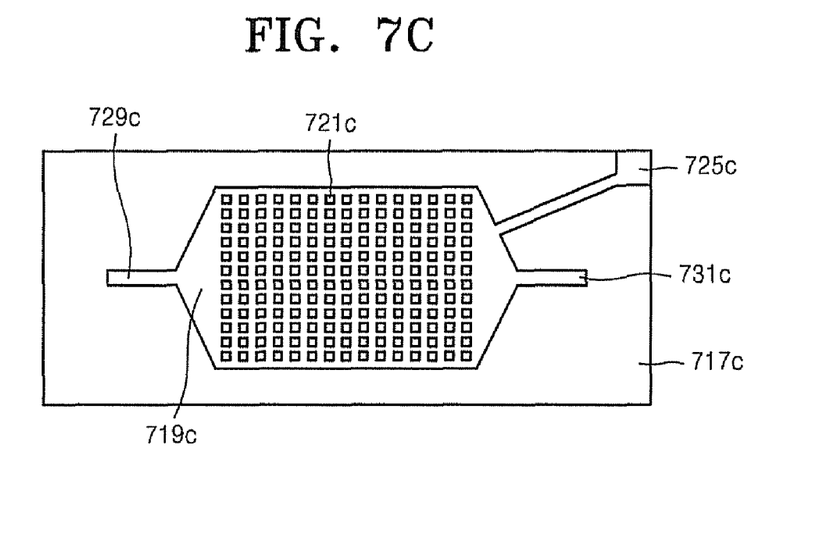

FIG. 7B and FIG. 7C are diagrams illustrating exemplary embodiments of upper sides of the cathode chamber substrates of different shapes that were produced in Example 2 and Example 3, respectively.

Referring to FIG. 7B, a plurality of pillars 721b are formed on the cathode chamber substrate 717b, a cathode electrode 719b is formed on a bottom of the cathode chamber in addition to the pillars 721b, and a cathode electrode pad 725b that may be connected to a power supply (not shown) is provided. The cathode chamber substrate 717b further includes an inlet 729b and an outlet 731b.

Referring to FIG. 7C, a plurality of pillars 721c are formed on the cathode chamber substrate 717c, a cathode electrode 719c is formed on a bottom of the cathode chamber in addition to the pillars 721c, and a cathode electrode pad 725c that may be connected to a power supply (not shown) is provided. The cathode chamber substrate 717c further includes an inlet 729c and an outlet 731c.

COMPARATIVE EXAMPLE 1

Production of Microfluidic Device

A microfluidic device was produced in the same manner as in Example 1, except that the first adhesive layer and the second adhesive layer were not provided therein.

EXPERIMENTAL EXAMPLE 1

Confirmation of the Effects of a Microfluidic Device on Concentration of a Sample Containing Cells The effects of capturing cells using the microfluidic devices produced in Examples 1 through 6 and Comparative Example 1 on the concentration of a sample containing cells were confirmed.

A 500 µl solution containing *Escherichia coli* cells at a cell concentration of $2.5 \times 10^6$ cells/ml flowed through the cathode chamber of each of the microfluidic devices at a rate of 30 µl/min, and then the number of cells captured in the cathode chamber was counted to determine a cell capture ratio.

The results are presented in Table 1. As shown in Table 1, the cell capture ratios obtained using the microfluidic devices produced in the Examples of the present invention were higher than 90%. It was found that when cells were captured by mechanically adjoining the upper faces of the pillars of a microfluidic device without bonding the upper faces of the pillars with an adhesive, no cells were captured.

TABLE 1

| Example 1 | Example 2 | Example 3 | Example 4 | Example 5 | Example 6 | Average | Standard deviation | Comp. Ex. 1 |
|---|---|---|---|---|---|---|---|---|
| 89.61% | 89.24% | 90.53% | 90.45% | 90.49% | 90.23% | 90.1% | 0.5 | App. 0% |

EXPERIMENTAL EXAMPLE 2

Confirmation of the Effects of Using a Microfluidic Device for DNA Extraction

The effects of using the microfluidic devices produced in Examples 1 through 3 and Comparative Example 1 for DNA extraction were examined.

A 500 µl solution containing *Escherichia coli* cells flowed through the cathode chamber of each of the microfluidic devices at a rate of 300 µl/min, subsequently 10 µl of a 55 millimoles (mM) solution of $Na_2SO_4$ was introduced to the anode chamber, and then an electric current of 2 milliamperes (mA) was applied through the cathode electrode and the anode electrode for 30 seconds. After completing electrolysis as described above, 20 µl of a 55 mM solution of $Na_2SO_4$ was introduced to the cathode chamber in order to recover the solution remaining in the cathode chamber. Subsequently, the recovered solution was used to perform a PCR reaction and electrophoresis under the same conditions. The DNA concentration was measured using a Lab Chip.

Figure 8:
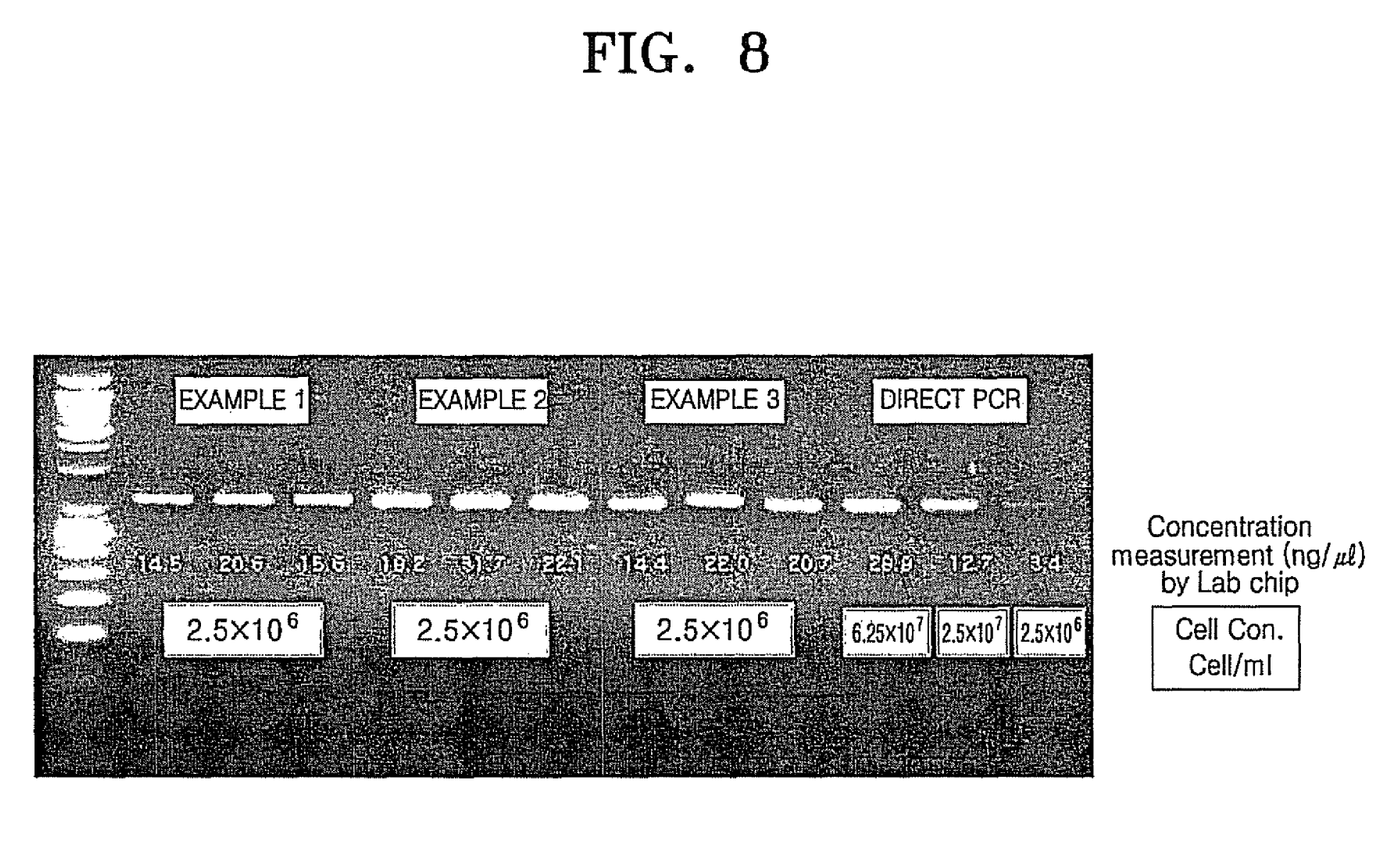
FIG. 8 is a photographic image obtained by electrophoresis performed in an Experimental Example such that the photographic image illustrates the effects of extracting DNA using a microfluidic device according to the present invention for DNA extraction.

FIG. 8 is a photographic image obtained by the electrophoresis performed in Experimental Example 2. The image illustrates the results of an effect of extracting DNA using the microfluidic device according the present invention on DNA extraction.

Referring to FIG. 8, as a result of repeating a PCR reaction three times using *E. coli* cells at a cell concentration of $2.5 \times 10^6$ cells/ml and using the microfluidic device of Example 1, the concentrations of DNA obtained were 14.5 nanograms per microliter (ng/µl), 20.6 ng/µ2*l* and 15.6 ng/µl. Furthermore, the concentrations of DNA obtained in the same manner using the microfluidic device of Example 2 were 19.2 ng/µl, 31.7 ng/µl and 22.1 ng/µl, and the concentrations of DNA obtained in the same manner using the microfluidic device of Example 3 were 14.4 ng/µl, 22.0 ng/µl and 20.7 ng/µl.

The term "direct PCR" refers to the results obtained by immediately performing a PCR reaction without introducing the same amount of solution containing *E. coli* cells into the microfluidic device. The concentration of DNA obtained with a solution at a cell concentration of $2.5 \times 10^6$ cells/ml was 3.4 ng/µl, the concentration of DNA obtained with a solution at a cell concentration of $2.5 \times 10^7$ cells/ml was 12.7 ng/µl, and the concentration of DNA obtained with a solution at a cell concentration of $6.25 \times 10^6$ cells/ml was 29.9 ng/µl.

From the results, it was found that the average concentration of extracted DNA obtained with solutions at the same concentration, namely, $2.5 \times 10^6$ cells/ml, was 20.09 ng/µl, for which in comparison was significantly higher than the DNA concentration of 3.4 ng/µl obtained by performing a direct PCR reaction using a solution at the same cell concentration.

Accordingly, it can be seen that the microfluidic device according to the illustrated embodiments can substantially simultaneously and effectively perform concentration of a sample containing cells or viruses and lysis of the cells or viruses.

As in the illustrated exemplary embodiments, the microfluidic device can effectively perform concentration of a sample containing cells or viruses and lysis of the cells or viruses, and can perform the processes of concentrating and lysis in a single chamber. Advantageously, the size of a lab-on-a-chip can be reduced by using the microfluidic device and a method of concentrating a sample containing cells or viruses and lysing the cells or viruses using the microfluidic device of the illustrated embodiments.

Furthermore, when the phenomenon of the chamber dividing membrane swelling is reduced or effectively prevented, and the change in the chamber volume is decreased, a sample of a predetermined volume can be readily introduced into the chamber. When the anode electrode is substantially (e.g., relatively widely) distributed in a ladder shape, the flow of electric current flows more easily, and pH adjustments can be performed efficiently.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microfluidic device for concentrating a sample including cells or viruses and lysing the cells or viruses, the device comprising:
   an anode chamber including an anode electrode;
   a cathode chamber including: a cathode electrode; and
   a plurality of a solid support completely within the cathode chamber; and
   an ion exchange membrane separating the anode chamber and the cathode chamber.

2. The microfluidic device of claim 1, wherein a surface of each of the solid supports is coated with a cell-binding substance.

3. The microfluidic device of claim 2, wherein the cell-binding substance is a hydrophobic substance having a water contact angle of about 70° to 90°, or is a charge donor substance.

4. The microfluidic device of claim 3, wherein the hydrophobic substance is selected from the group consisting of octadecyltrichlorosilane (OTS), tridecafluorotetrahydrooctyl trimethoxysilane (DTS), octadecyldimethyl(3-trimethoxysilylpropyl)ammonium chloride (OTC), polyethyleneiminetrimethoxysilane (PEIM) and mixtures thereof.

5. The microfluidic device of claim 1, wherein the solid support has a structure selected from the group consisting of a flat structure, a pillar structure, a bead structure and a sieve structure.

6. The microfluidic device of claim 1, wherein the ion exchange membrane conducts electric current, but does not allow permeation of ions and gases that are generated by electrolysis in the anode chamber and the cathode chamber.

7. The microfluidic device of claim 1, wherein the cathode electrode includes a metal able to absorb hydrogen gas and the anode electrode includes a metal having a higher standard oxidation potential than that of water and does not react with water.

8. The microfluidic device of claim 7, wherein the cathode electrode is formed of palladium (Pd).

9. The microfluidic device of claim 7, wherein the anode electrode is formed of a metal selected from the group consisting of copper (Cu), lead (Pd), silver (Ag), chromium (Cr), titanium (Ti), nickel (Ni), zinc (Zn), iron (Fe) and tin (Sn).

10. The microfluidic device of claim 1, wherein the cathode chamber and the anode chamber, respectively, each further includes an inlet and an outlet through which a solution is introduced and discharged.

11. The microfluidic device of claim 1, further comprising
a first adhesive layer formed on a first side of the ion exchange membrane;
a second adhesive layer formed on a second side of the ion exchange membrane, the second side being opposite to the first side;
an anode electrode supporting substrate adhered to the first adhesive layer and including a ladder-shaped opening, the anode electrode fixed on the anode electrode supporting substrate and corresponding in shape with the ladder shape of the opening of the anode electrode supporting substrate;
an anode chamber substrate forming the anode chamber while covering the anode electrode;
a cathode chamber substrate adhered to the second adhesive layer and forming the cathode chamber, the cathode chamber including each of the solid supports having an upper surface adhered to the second adhesive layer; and
the cathode electrode fixed on a bottom of the cathode chamber.

12. The microfluidic device of claim 11, wherein the first adhesive layer and the second adhesive layer conduct electric current.

13. The microfluidic device of claim 11, wherein the anode electrode supporting substrate is formed of printed circuit boards ("PCBs").

14. A method of producing a microfluidic device, the method comprising
producing an anode electrode supporting substrate including a ladder-shaped anode electrode on one side and an opening corresponding in shape with the ladder-shaped anode electrode;
fixing an anode chamber substrate on the anode electrode supporting substrate, covering the anode electrode and forming an anode chamber;
producing a cathode chamber substrate including a solid support, forming a cathode chamber and including a cathode electrode fixed on a bottom of the cathode chamber;
forming a first adhesive layer and a second adhesive layer on respective sides of an ion exchange membrane; and
adhering the anode electrode supporting substrate on the first adhesive layer and adhering the cathode chamber substrate on the second adhesive layer;
wherein the microfluidic device comprises:
the anode chamber including the anode electrode;
the cathode chamber including the cathode electrode; and
the ion exchange membrane separating the anode chamber and the cathode chamber,
wherein the cathode chamber includes the solid support.

15. The method of claim 14, wherein the producing an anode electrode supporting substrate comprises:
coating a photoresist film on a metal-coated printed circuit board ("PCB");
irradiating ultraviolet ("UV") light through a mask having a pattern designed to form the ladder-shaped anode electrode, and developing the pattern on the anode electrode exposing the metal-coated PCB;
etching the exposed metal coated PCB; and
cutting the exposed metal PCB to form the opening.

16. The method of claim 14, wherein the producing a cathode chamber substrate comprises:
coating a photoresist film on a solid substrate;
irradiating UV light through a mask having a pattern designed to form a solid support, and developing the pattern on the solid substrate exposing the solid substrate;
etching the exposed solid substrate;
vapor depositing a metal on the solid substrate by vacuum evaporation involving heat with an electron beam;
removing the photoresist film; and
electroplating a metal-deposited side of the solid substrate with another metal.

17. The method of claim 14, wherein the producing a cathode chamber substrate further comprises coating a surface of the solid support with a cell-binding substance.

18. The method of claim 14, wherein the forming first and second adhesive layers comprises:
spin coating an adhesive on respective sides of the ion exchange membrane;
adhering one side of the ion exchange membrane to the anode supporting substrate while spreading the ion exchange membrane using a roller; and
bonding an opposing side of the ion exchange membrane to the cathode chamber substrate.

19. The method of claim 18, wherein the adhesive is liquid at room temperature and attains adhesiveness while being cured when heat or UV light is applied to the adhesive.

20. The method of claim 14, wherein the adhesion of first and second adhesive layers to the anode electrode supporting substrate and the cathode chamber substrate includes arranging the anode electrode supporting substrate, the ion exchange membrane and the cathode chamber substrate in an array, and applying heat and pressure to the array.

21. A method of concentrating a sample including cells or viruses and lysing the cells or viruses using a microfluidic device, the method comprising:
introducing a solution including ions having a standard oxidation potential higher or lower than that of water, into an anode chamber of the micro fluidic device;
introducing a solution including cells or viruses and ions having a lower standard reduction potential than that of water into a cathode chamber of the microfluidic device; and
applying electric current through an anode electrode and an cathode electrode inducing electrolysis in the anode chamber and the cathode chamber and adjusting the pH of the solution introduced into the anode chamber or the cathode chamber;
wherein the microfluidic device comprises:
the anode chamber including the anode electrode;
the cathode chamber including the cathode electrode and a plurality of a solid support disposed completely within the cathode chamber; and
an ion exchange membrane separating the anode chamber and the cathode chamber.

22. The method of claim 21, wherein the ions that are introduced into the anode chamber and have a lower standard oxidation potential than that of water include at least one selected from the group consisting of $NO_3^-$, $F^-$, $SO_4^{2-}$, $PO_4^{3-}$ and $CO_3^{2-}$.

23. The method of claim 21, wherein the ions that are introduced into the anode chamber and have a higher standard oxidation potential than that of water include $Cl^-$.

24. The method of claim 21, wherein the ions that are introduced into the cathode chamber and have a lower standard reduction potential than that of water include at least one selected from the group consisting of $Na^+$, $K^+$, $Ca^{2+}$, $Mg^{2+}$ and $Al^{3+}$.

25. The method of claim 21, wherein the pH of the solutions is adjusted by varying the direction of the applied electric current, the intensity of the applied electric current, the duration of the applied electric current, the width of the electrode, or the thickness of the ion exchange membrane.

* * * * *